US007876936B2

(12) United States Patent
Raffy

(10) Patent No.: US 7,876,936 B2
(45) Date of Patent: Jan. 25, 2011

(54) METHOD FOR SEGMENTING ARTERIES AND VEINS

(75) Inventor: Philippe Raffy, Sunnyvale, CA (US)

(73) Assignee: MeVis Medical Solutions, Inc., Pewaukee, WI (US)

( * ) Notice: Subject to any disclaimer, the term of this patent is extended or adjusted under 35 U.S.C. 154(b) by 993 days.

(21) Appl. No.: 11/344,833

(22) Filed: Jan. 31, 2006

(65) Prior Publication Data
US 2007/0177785 A1   Aug. 2, 2007

(51) Int. Cl.
*G06K 9/00* (2006.01)
(52) U.S. Cl. ..................................... 382/128
(58) Field of Classification Search ............... 382/128, 382/131, 132; 600/407
See application file for complete search history.

(56) References Cited

U.S. PATENT DOCUMENTS

| | | | |
|---|---|---|---|
| 2004/0120557 A1 | 6/2004 | Sabol et al. | |
| 2004/0223633 A1* | 11/2004 | Krishnan | 382/128 |
| 2005/0240094 A1* | 10/2005 | Pichon et al. | 600/407 |
| 2005/0249399 A1* | 11/2005 | Tek et al. | 382/154 |
| 2005/0256400 A1* | 11/2005 | Raman et al. | 600/425 |
| 2006/0056685 A1* | 3/2006 | Kiraly et al. | 382/165 |
| 2006/0056691 A1* | 3/2006 | Vaz et al. | 382/173 |
| 2007/0058870 A1* | 3/2007 | Liang et al. | 382/190 |
| 2007/0160271 A1* | 7/2007 | Doi et al. | 382/128 |

OTHER PUBLICATIONS

Tianhu Lei; Udupa, J.K.; Saha, P.K.; Odhner, D.; , "Artery-vein separation via MRA—An image processing approach," Medical Imaging, IEEE Transactions on , vol. 20, No. 8, pp. 689-703, Aug. 2001 URL: http://ieeexplore.ieee.org/stamp/stamp.jsp?tp=&arnumber=938238&isnumber=20309.*

* cited by examiner

*Primary Examiner*—John B Strege
*Assistant Examiner*—Nirav G Patel
(74) *Attorney, Agent, or Firm*—Quarles & Brady LLP

(57) ABSTRACT

In a preferred embodiment a radiologist traces the pulmonary artery and pulmonary veins visible in a set of CT images and identifies the arteries and veins. The radiologist's identification of the pulmonary arteries and pulmonary veins is then received by an image analyzer and combined with the analyzer's identification of the pulmonary arteries to form a combined identification; and the analyzer then reviews this combined identification of the pulmonary arteries to detect any pulmonary embolisms. The radiologist's identification of any pulmonary embolisms is compared with the analyzer's identification of any pulmonary embolisms to determine if there are any embolisms identified by the analyzer that were not identified by the radiologist.

9 Claims, 5 Drawing Sheets

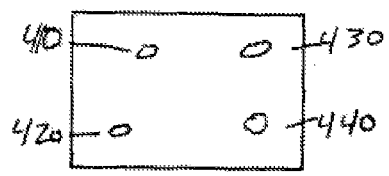
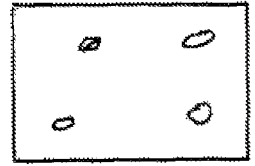
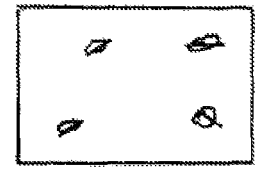
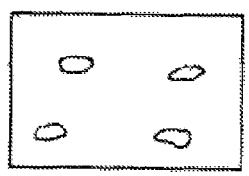
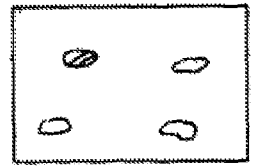
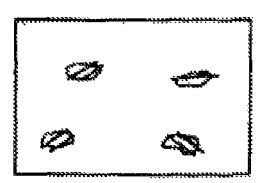
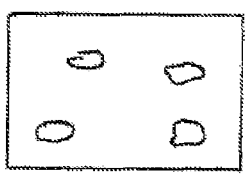
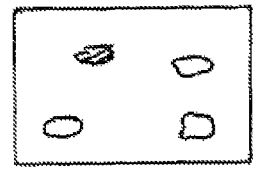
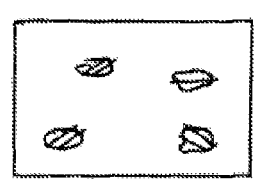
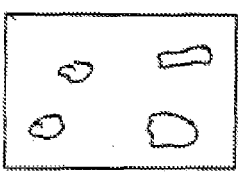
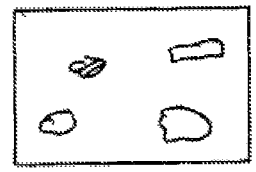
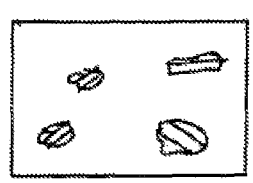
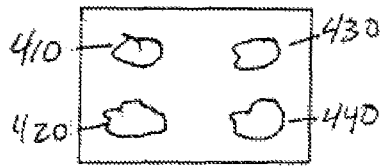
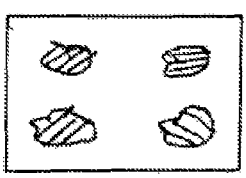
FIG. 4A        FIG. 4B        FIG. 4C

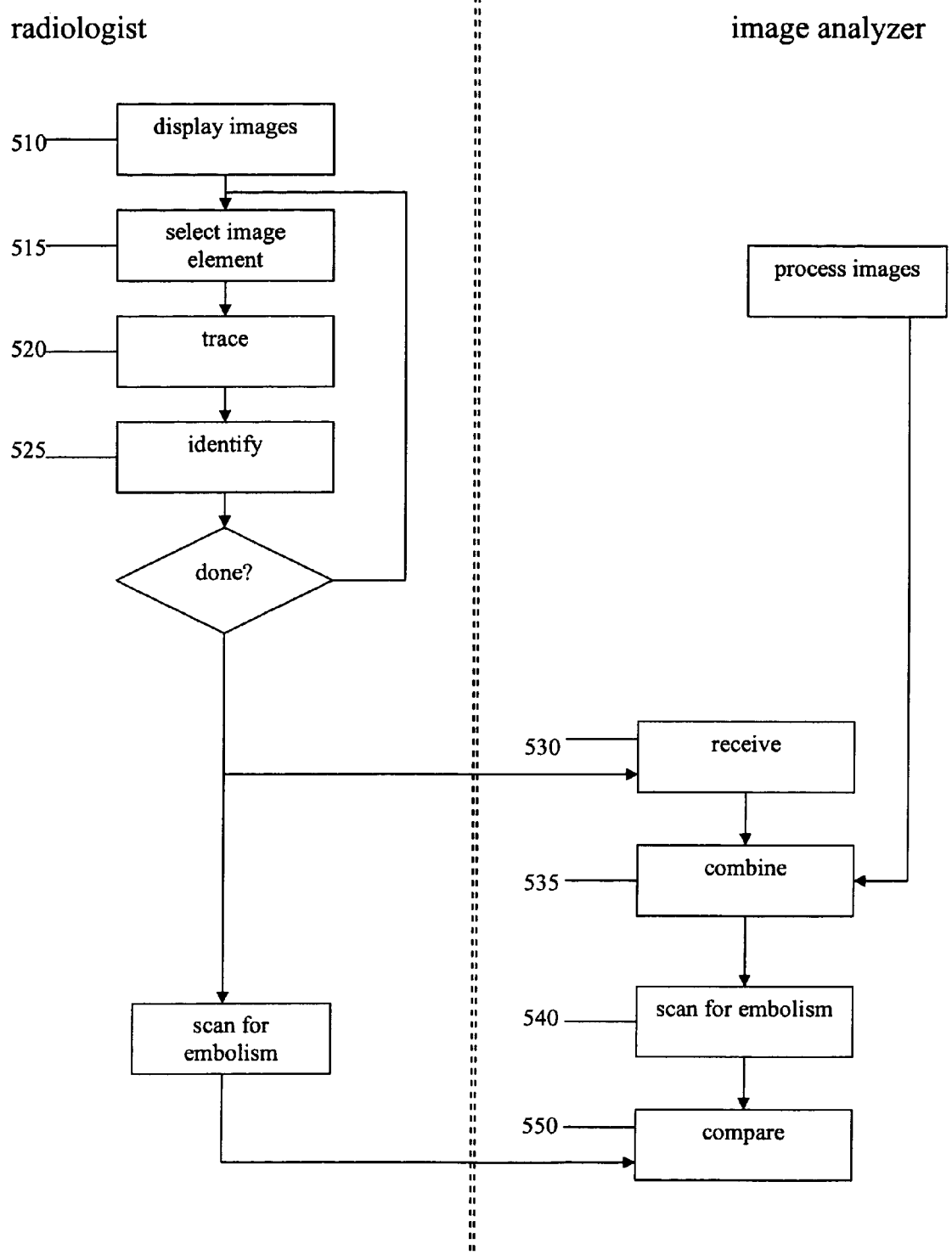

METHOD FOR SEGMENTING ARTERIES AND VEINS

FIELD OF THE INVENTION

This relates to improvements in computer-aided methods for detecting pulmonary embolisms in computer tomography (CT) images.

BACKGROUND OF THE INVENTION

A pulmonary embolism is a blood clot that has lodged in one of the pulmonary arteries between the heart and the lungs. Typically, the clot formed in one of the major veins such as one of the leg veins, broke lose from its point of formation, traveled through the veins to the heart and was pumped by the heart into the pulmonary arteries. The pulmonary arteries are a tree-like structure extending from the heart to the left and right lungs. The pulmonary arteries continually decrease in size from the heart to the lungs and eventually the blood clot lodges at a point where the lumen of the artery is no longer wider than the blood clot. FIG. 1 illustrates an embolism 100 that has lodged at a point in the artery 110 where the lumen is no longer wide enough to let it pass.

In the lungs, carbon dioxide carried by the blood from the pulmonary arteries is exchanged for oxygen. The oxygen-enriched blood is returned to the heart via the pulmonary veins for distribution to the rest of the body. The pulmonary veins are a tree-like structure similar to the pulmonary arteries; and most images of the pulmonary veins as seen in a typical CT image section are indistinguishable from images of the pulmonary arteries.

To locate a pulmonary embolism using CT, a contrast agent is injected into the blood stream and a CT scan is made of the pulmonary region. The CT scan produces a series of images of sections of the pulmonary region, perhaps as many as 200 such images. The embolism will appear in the series of CT images as a point in a vessel structure that has a brighter region on one side of the point than on the other side. Four such CT images are shown in FIGS. 2A-2D. In each case the pulmonary embolism is circled. The change in contrast arises because the embolism prevents the contrast agent from flowing beyond the point in the artery where the embolism has lodged.

It is advantageous to be able to read a series of CT sections using computer-aided detection techniques. In present practice, such a reading provides "a second look" or a check on an independent reading made by a radiologist. Such a reading is performed by the computer by using a region growing technique to proceed along the pulmonary arteries from the heart to the lungs looking for a point where there is an abrupt change in the gray scale of the image. Unfortunately, with presently available algorithms it is sometimes difficult for the computer to distinguish between the pulmonary arteries that must be read and the pulmonary veins that do not have to be read. As a result, pulmonary veins may be incorrectly found to be arteries (false positives) by CAD and are read anyway with considerable increase in the total time required to complete a reading.

SUMMARY OF THE INVENTION

The present invention aims to speed up the process of computer reading of a series of CT pulmonary sections by using some of the radiologist's efforts in reading these sections. In particular, in the course of reading the CT sections, the radiologist will typically distinguish between the pulmonary arteries and pulmonary veins. He/she ordinarily does this by marking the arteries and veins as he/she scans through a set of CT sections. This marking conceivably could be done mentally but as a practical matter the CT sections are presently reviewed on a computer terminal and it is common practice to mark the individual arteries and veins using a cursor and mouse clicks. Thus, a radiologist reviews a set of CT sections by selecting an image of a vein or artery in one CT section and following it through the other CT sections, moving the cursor to mark successive images of the selected vein or artery on successive CT sections. After tracing one vein or artery through the set of CT sections, the radiologist then repeats the process for every other vein and artery present in the CT sections. Whether the vessel being traced is an artery or a vein can usually be determined from its relationship with the heart in the CT sections that reveal that relationship. And once the vessel has been identified as a pulmonary vein it is ignored by the radiologist since no embolism can reach a vein. By proceeding in this fashion, the radiologist is able to assure himself/herself that all the pulmonary arteries have been reviewed. And in this process he/she has identified all the pulmonary arteries and distinguished them from the pulmonary veins.

In accordance with the invention, the radiologist's identification of the pulmonary arteries and pulmonary veins is received by the computer and is combined with any processing the computer has performed on the CT pulmonary section to form a combined identification of the pulmonary arteries; and the computer then reviews this combined identification of the pulmonary arteries to detect any pulmonary embolisms.

Finally, the radiologist's identification of any pulmonary embolisms is compared with the computer's identification of any pulmonary embolisms to determine if there are any embolisms identified by the computer that were not identified by the radiologist.

BRIEF DESCRIPTION OF DRAWINGS

These and other objects, features and advantages of the invention will be more readily apparent from the following Detailed Description in which:

FIGS. 4A, 4B and 4C depict the marking of a series CT section by a radiologist, and FIG. 5 is a flowchart depicting an illustrative method of the invention.

DETAILED DESCRIPTION

Figure 1:
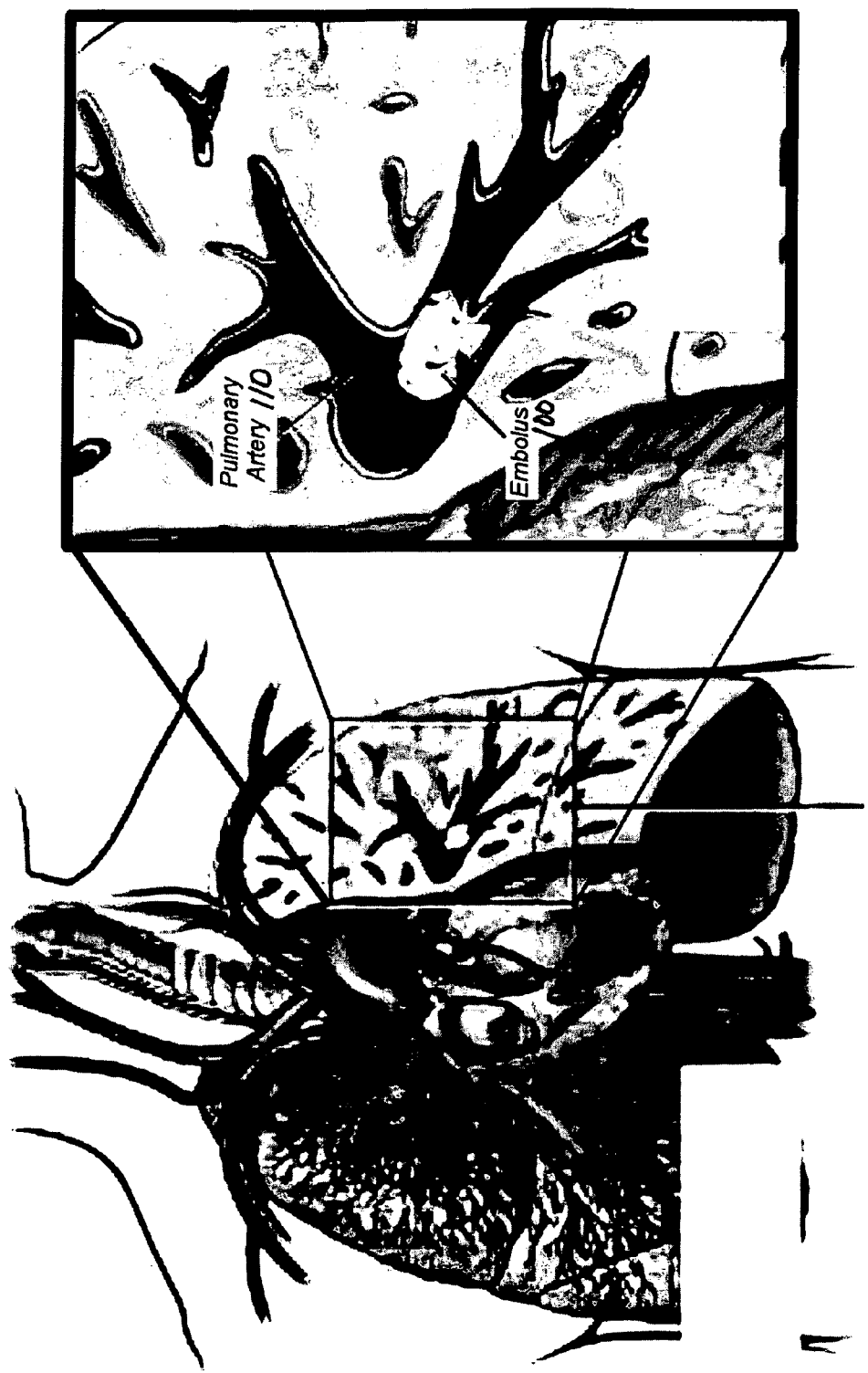
FIG. 1 is a schematic illustration of a pulmonary embolism.
Figure 2:
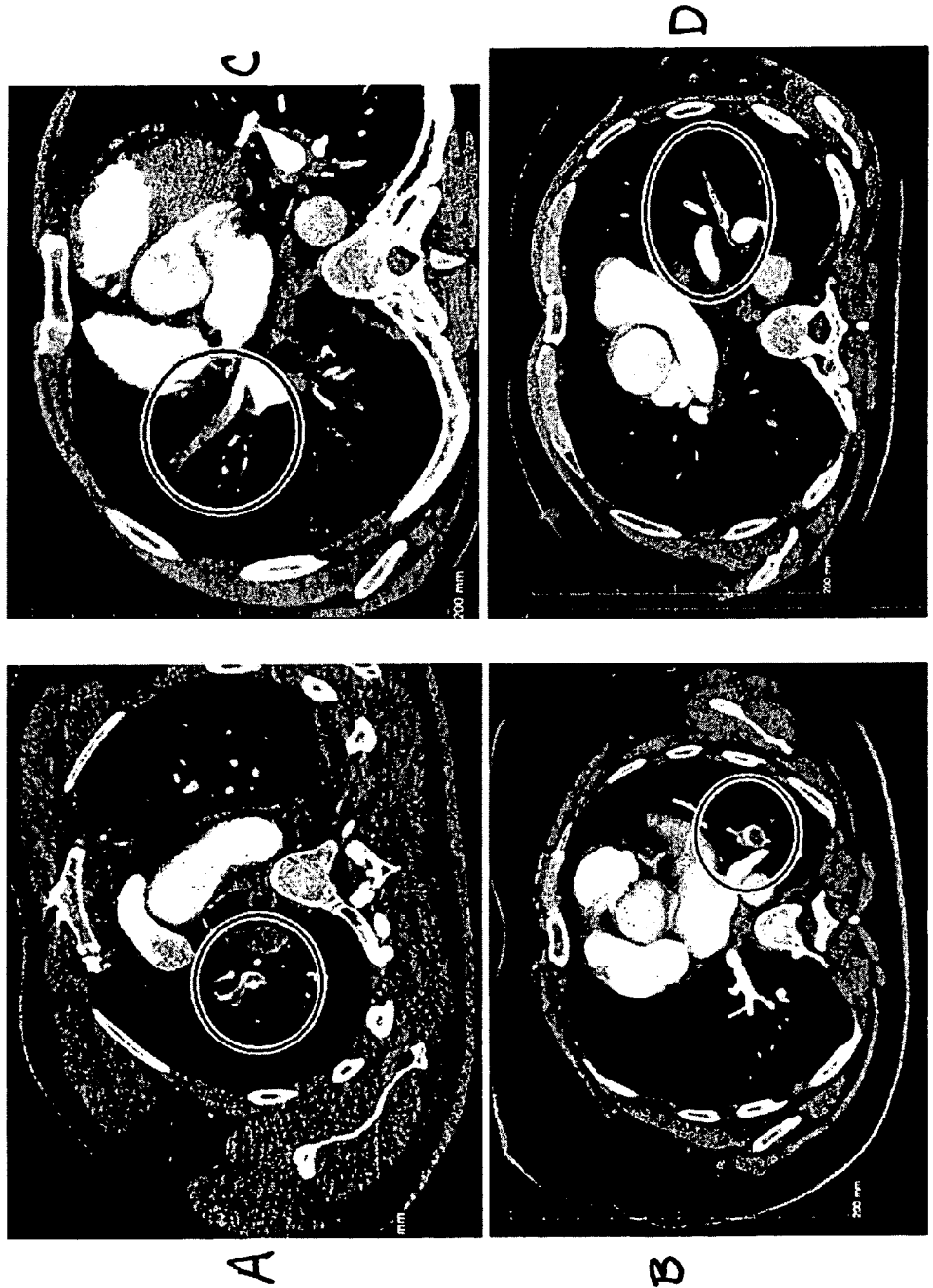
FIGS. 2A-2D are CT images of pulmonary embolisms.
Figure 3:
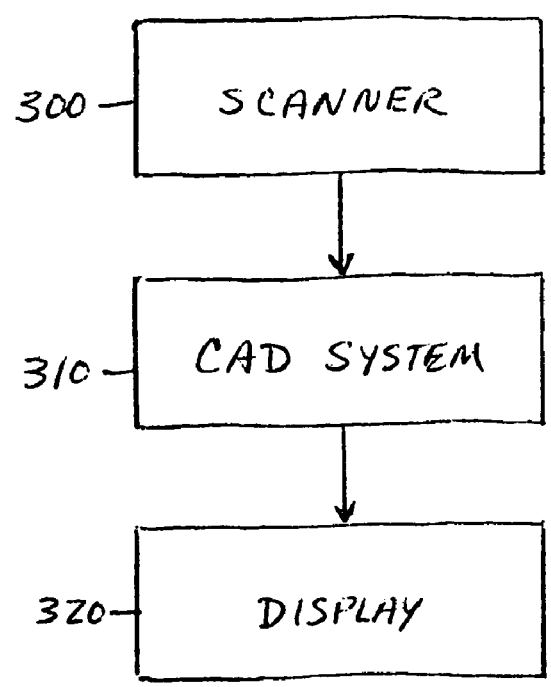
FIG. 3 is a schematic illustration of apparatus used in the practice of the invention.

FIG. 3 depicts illustrative apparatus used in the practice of the invention. The apparatus includes a multi-slice computer tomography (MSCT) scanner 300, a CAD system 310, and an input/output (I/O) system 320. The MSCT scanner is a commercially available device made by companies such as General Electric and Siemens. The CAD system 310 is a personal computer or a work station running software that analyzes the CT images produced by the MSCT scanner in accordance with the present invention. The I/O system 320 comprises a display and appropriate input devices such as a cursor and mouse or other tracking device.

To trace the pulmonary arteries and veins, the radiologist is provided with a set of CT sections of the pulmonary region. There may be up to 200 or so such sections. In the past, the sections would be recorded on film and the radiologist would trace the arteries and veins from one film image to another. To ensure that each vessel was traced, it was customary to mark off the vessels in each image as they were traced. With modern digital CT scanners, the CT image sections are digital images and it is efficient to display them on a computer display. In such an arrangement, the marking can be done by moving a cursor along the vessel being traced and clicking on a mouse when the cursor intercepts the image of the vessel being traced.

In tracing the arteries and veins, the radiologist normally works along these vessels moving from the lungs toward the heart. When the tracing effort reaches the region near the heart, the radiologist can usually determine from the relationship between the vessel and the heart whether the vessel is an artery or a vein and identifies the vessel accordingly. Alternatively, the vessel being traced merges with another vessel that has been previously identified as an artery or a vein and that identification is applied to the vessel being traced. By working along the vessel from the lungs toward the heart, the radiologist is able to follow a single vessel without having to keep track of the various vessels that branch off from it.

FIGS. 4A, 4B, 4C depict in highly schematic form the radiologist's tracing of arteries and veins in a series of CT sections of the pulmonary region. Each of FIGS. 4A, 4B and 4C is a set of five schematic images labeled (1)-(5). The five images schematically illustrate the same four vessels 410, 420, 430, 440 at five points along the way between the heart and the lungs. The set of images in FIGS. 4A, 4B and 4C are the same except that the set of FIG. 4A represents the images before any tracing is done; the set of FIG. 4B represents the images after one vessel is traced; and the set of FIG. 4C represents the images after all four vessels have been traced.

When the radiologist is provided with a series of CT images as represented by the set of FIG. 4A, he/she moves the cursor to intercept one of the images of a vessel and clicks on the mouse when it does. The analyzer software remembers the location of the mouse at the time of the click and changes the display at that point in some recognizable way. Illustratively, the color of the vessel that was intercepted by the mouse might be changed. Alternatively, the shading or cross-hatching of the vessel might be changed. For purposes of illustration in FIGS. 4B and 4C, the cross-hatching of the vessels is changed. In particular, FIG. 4B represents the five image sections after the radiologist has finished tracing one of the vessels and the analyzer software has finished changing the display. As noted above, the tracing is made in the direction of the heart and the radiologist is able to determine from the relation of the traced vessel to the heart whether the traced vessel is an artery or a vein. This determination is entered into the system.

The tracing process is continued with each vessel image in each image section being selected and marked in the display and traced in additional image sections until it joins another vessel or the heart. In each case, upon completion of a tracing, a determination is made whether the vessel is an artery or a vein and this determination is retained in system memory. Advantageously, whether a vessel has been determined to be an artery or a vein it is also displayed perhaps using different colors, different shading or different cross-hatching. For example, in FIG. 4C the vessel 440 being traced is depicted with cross-hatching of a first type, vessels 410 and 420 are depicted with cross-hatching of a second type representing arteries, and vessel 430 is depicted with cross-hatching of a third type representing a vein.

When the computer traces arteries and veins, the tracing algorithm typically starts at the heart, which is easy to locate, and works toward the lungs. The algorithm used is typically a region growing algorithm that is well-suited to keeping track of the branching of the vessel being tracked. Unfortunately, as noted above, it is difficult for the computer's tracing algorithm to distinguish between arteries and veins and as a result many pulmonary veins are falsely identified as pulmonary arteries. As a result, when examining the pulmonary arteries for embolisms, the computer algorithm will typically examine needlessly many arteries that, in fact, are veins where no pulmonary embolism can be located, thereby increasing the time required to conduct the search for the embolisms.

In accordance with the present invention, the radiologist's determination of which pulmonary vessels are arteries and which are veins is used by the computer to reduce the number of vessels to be examined for pulmonary embolisms.

FIG. 5 is a flow chart depicting an illustrative implementation of the invention. At step 510 the set of CT sections of an individual's pulmonary region is presented on the display of I/O system 320 for review by a radiologist. At step 515 the radiologist selects an image of an artery or vein in one of the CT sections; and at step 520 he/she traces the vessel through the set of CT sections until at step 525 it can be identified as an artery or vein. In the case of the first tracing, the tracing will most likely go all the way back to the region near the heart before the radiologist can determine if the vessel is an artery or a vein. In the case of subsequent tracings, whether the vessel is an artery or vein may be resolved by observing its merger with a previously identified artery or vein.

The radiologist repeats steps 515, 520, 525 of selecting an image of a previously untraced vessel, tracing the image and identifying the vessel until all the images have been traced and identified.

At step 530, the tracings completed by the radiologist are received by analyzer 310 and combined by analyzer 310 with whatever analysis has been performed by the analyzer on the same set of CT sections. In some cases, the analyzer may have performed a complete analysis of the pulmonary vessels shown in the CT sections and produced its own determination as to which vessels are arteries and which are veins. In this case, any differences between the analyzer's determination and the radiologist's determination are brought to the radiologist's attention for resolution. For example, the differences may be noted on a computer display of the vascular tree structure.

Alternatively, the analyzer may limit its processing to a determination of the vascular tree structure and make no effort to identify whether pulmonary vessels are arteries or veins. In this case, the radiologist's determinations are simply applied to the elements of the vascular tree structure completed by the analyzer.

Still another possibility would be that the analyzer simply accepts the tracings and determinations made by the radiologist.

After combining the input from the radiologist with whatever processing it has done, the analyzer then scans the images of the arteries at step 540 to detect any embolisms. This scanning process is performed using known algorithms for detecting embolisms in the images of the pulmonary arteries.

Finally, at step 550, the radiologist's reading of the CT sections is compared with the analyzer's reading of the CT sections to provide a second look at the radiologist's reading of the CT sections. This comparison can be done in several ways. For example, the analyzer can generate a visual image of the artery tree with indications where it has determined embolisms to be located and the radiologist can compare this with his/her own opinion as to where the embolisms are located and accept or revise any determinations. Alternatively, the radiologist's opinion can be entered onto the digital CT image sections on the display by using the cursor and mouse to indicate his/her opinion as to the location of each embolism on the CT section where it appears. These indications can then be transferred to the analyzer and the analyzer can then display a visual image of the artery tree with both the radiologist's opinion and the analyzer's determinations set forth on the tree. The radiologist can then accept or revise any of the opinions and determinations.

As will be apparent to those skilled in the art, numerous variations may be practiced within the spirit and scope of the invention.

What is claimed is:

1. A computer-implemented method of processing a series of computed tomography (CT) sections of a pulmonary region to separate pulmonary arteries from pulmonary veins comprising:
   receiving a first identification of vessels of the pulmonary region from a user interface device, the first identification identifying each of the vessels as one of the pulmonary arteries and pulmonary veins visible in each of the CT sections and including a tracing of each of the vessels of the pulmonary region through one or more of the CT sections, by:
      displaying each of the series of CT sections of the pulmonary region using the user interface device,
      receiving a tracing of the vessels of the pulmonary region through each of the series of CT sections using the user interface, and
      receiving an identification of each of the vessels of the pulmonary region as one of the pulmonary arteries and pulmonary veins using the user interface;
   performing a computer-aided identification of vessels of the pulmonary region to provide a second identification of vessels of the pulmonary region using a region growing algorithm, the second identification identifying each of the vessels as one of the pulmonary arteries and pulmonary veins in each of the CT sections and the computer-aided identification being implemented without using the first identification;
   combining the first identification with the second identification to produce a combined identification of the pulmonary arteries and pulmonary veins and detect differences between the first and second identification;
   using the combined identification of the pulmonary arteries and pulmonary veins to segment the pulmonary arteries from the pulmonary veins; and
   displaying the differences between the first and second identification using the user interface device.

2. The method of claim 1 further comprising the step of scanning the pulmonary arteries for an embolism.

3. The method of claim 2 further comprising the step of comparing a location of a pulmonary embolism identified by a radiologist with a location of a pulmonary embolism identified by the scanning step.

4. A computer-implemented method of processing a series of computed tomography (CT) sections of a pulmonary region to separate pulmonary arteries from pulmonary veins comprising:
   receiving a first identification of vessels of the pulmonary region from a user interface device, the first identification identifying each of the vessels as one of the pulmonary arteries and pulmonary veins visible in the CT sections, by:
      displaying each of the series of CT sections of the pulmonary region using the user interface device,
      receiving a tracing of the vessels of the pulmonary region through each of the series of CT sections using the user interface, and
      receiving an identification of each of the vessels of the pulmonary region as one of the pulmonary arteries and pulmonary veins using the user interface;
   performing a computer-aided identification of vessels of the pulmonary region to provide a second identification of vessels of the pulmonary region, the second identification identifying each of the vessels as one of the pulmonary arteries and pulmonary veins in the CT sections;
   combining the first and second identification to produce a combined identification of the pulmonary arteries and pulmonary veins; and
   using the combined identification of the pulmonary arteries and pulmonary veins to segment the pulmonary arteries from the pulmonary veins.

5. The method of claim 4 further comprising the step of scanning the pulmonary arteries for an embolism.

6. The method of claim 5 further comprising the step of comparing a location of a pulmonary embolism identified by a radiologist with a location of a pulmonary embolism identified by the scanning step.

7. A method of computer processing a series of computed tomography (CT) sections of a pulmonary region to separate pulmonary arteries from pulmonary veins comprising:
   receiving a first tracing of vessels of the pulmonary region through the series of CT sections, the first tracing identifying each vessel as either a pulmonary artery or a pulmonary vein visible in the CT sections from a user interface;
   using the first tracing to identify the pulmonary arteries and pulmonary veins in a computer-generated representation of the pulmonary arteries and veins;
   using the identification of the pulmonary arteries and pulmonary veins from the first tracing to segment the pulmonary arteries from the pulmonary veins; and
   scanning the pulmonary arteries for an embolism.

8. The method of claim 7 further comprising the step of comparing a location of a pulmonary embolism identified by a radiologist with a location of a pulmonary embolism identified by the scanning step.

9. A method for interactive computer-aided detection in a lung volume, comprising:
   a. automatically segmenting pulmonary artery tissue and pulmonary vein tissue from the lung volume;
   b. displaying a three-dimensional representation of the lung volume including the segmented pulmonary artery and pulmonary vein tissue;
   c. facilitating interactive tracing of a pulmonary artery tree of interest in the three dimensional representation;
   d. storing a set of points selected during the interactive tracing corresponding to points in the traced pulmonary artery tree; and
   e. performing automated abnormality detection only on vessels of the traced pulmonary artery tree, whereby the abnormality detection results are free of false positive detections that may be associated with pulmonary vein tissue.

* * * * *